United States Patent
Kaminskyj et al.

(10) Patent No.: US 8,598,083 B2
(45) Date of Patent: Dec. 3, 2013

(54) **METHOD FOR INCREASING PLANT GROWTH USING THE FUNGUS *TRICHODERMA HARZIANUM***

(75) Inventors: Susan Gail Willets Kaminskyj, Saskatoon (CA); James Frederick Basinger, Saskatoon (CA); Xiaohui Bao, Saskatoon (CA); Russell John Rodriguez, Seattle, WA (US); Regina Soon Redman, Seattle, WA (US)

(73) Assignees: University of Washington, Seattle, WA (US); University of Saskatchewan, Saskatchewan (CA)

( * ) Notice: Subject to any disclaimer, the term of this patent is extended or adjusted under 35 U.S.C. 154(b) by 0 days.

(21) Appl. No.: 13/395,765

(22) PCT Filed: Sep. 16, 2010

(86) PCT No.: PCT/CA2010/001454
§ 371 (c)(1),
(2), (4) Date: Mar. 13, 2012

(87) PCT Pub. No.: WO2011/032281
PCT Pub. Date: Mar. 24, 2011

(65) Prior Publication Data
US 2012/0178624 A1    Jul. 12, 2012

Related U.S. Application Data

(60) Provisional application No. 61/243,340, filed on Sep. 17, 2009.

(51) Int. Cl.
*A01N 63/00*    (2006.01)
*C12N 1/00*    (2006.01)

(52) U.S. Cl.
USPC ........ 504/117; 435/256.7; 435/945; 424/93.5

(58) Field of Classification Search
None
See application file for complete search history.

(56) References Cited

U.S. PATENT DOCUMENTS

| | | | |
|---|---|---|---|
| 4,828,600 | A | 5/1989 | McCabe et al. |
| 6,475,772 | B1 | 11/2002 | Kalra et al. |
| 7,273,552 | B2 | 9/2007 | Lynch |
| 2002/0103083 | A1 | 8/2002 | Harman |
| 2004/0261578 | A1 | 12/2004 | Harman et al. |
| 2008/0318777 | A1 | 12/2008 | Lin et al. |

FOREIGN PATENT DOCUMENTS

| | | |
|---|---|---|
| WO | WO95/20879 A2 | 8/1995 |
| WO | WO2007/110686 A2 | 10/2007 |
| WO | WO2009/009805 A1 | 1/2009 |

OTHER PUBLICATIONS

Al-Turki, A.I., "Microbial polycyclic aromatic hydrocarbons degradation in soil", Res. J. Env. Toxicol., 2009, vol. 3, No. 1, p. 1-8.

Berg, G. "Plant-microbe interactions promoting plant growth and health: perspectives for controlled use of microorganisms in agriculture", Appl. Microbiol. Biotechnol., Aug. 2009, vol. 84, p. 11-18.

Bois, G. et al., "Mycorrhizal inoculum potentials of pure reclamation materials and revegetated tailing sands from teh Canadian oil sand industry", Mycorrhiza, 2005, vol. 15, p. 149-158.

Chacon, M.R. et al., "Microscopic and transcriptome analyses of early colonization of tomato roots by *Trichoderma harzianum*", Intl Microbiology, 2007, 10:19-27.

Ezzi, M.I. and Lynch, J.M., "Plant microcosm studies demonstrating bioremediation of cyanide toxicity by *Trichoderma* and *Fusariuim* spp.", Bio Fertil Soils, 2005, 42:40-44.

Harman, G.E. et al., "*Trichoderma* species—opportunistic, avirulent plant symbionts", Nat. Rev. Microbiol., 2004, vol. 2, p. 43-56.

Harman, G.E. et al., "Interactions Between *Trichoderma harzianum* Strain T22 and Maize Inbred Line Mo17 and Effects of These Interactions on Diseases Caused by *Pythium ultimum* and *Colletotrichum graminicola*", Phytopathology, 2004, vol. 94, No. 2, p. 147-15.

Harman, G.E., "Overview of Mechanisms and Uses of *Trichoderma* spp.", Phytopathology, 2006, vol. 96, No. 2, p. 190-194.

Potin, O. et al., "Bioremediation of an aged polycyclic aromatic hyrocarbons (PAHs)-contaminated soil by filamentous fungi isolated from the soil", Int. Biodeteriod. Biodegrad., 2004, vol. 54, p. 45-52.

Shoresh, M. and Harman, G.E., "The Molecular Basis of Shoot Responses of Maize Seedlings to *Trichoderma harzianum* T22 Inoculation of the Root: A Proteomic Approach", Plant Physiology, 2008, vol. 147, p. 2147-2163.

Yedidia, I. et al., "Induction of Defence Responses in Cucumber Plants (cucumis sativus L.) by the Biocontrol Agent *Trichoderma harzianum*", Applied and Environmental Microbiology, 1999, vol. 65, No. 3, p. 1061-1070.

Donoso, E.P., et al. "Water Deficit as a Driver of the Mutualistic Relationship between the Fungus *Trichoderma harzianum* and Two Wheat Genotypes." Applied & Environmental Microbiology. Mar. 2008;74(5):1412-1417.

*Primary Examiner* — Jennifer McDonald
*Assistant Examiner* — Qing Xu
(74) *Attorney, Agent, or Firm* — Dann, Dorfman, Herrell & Skillman; Kathleen D. Rigaut

(57) ABSTRACT

A novel strain of *Trichoderma harzianum* called TSTh20-1 is described. TSTh20-1 is useful in promoting plant growth, increasing water use efficiency of plants and in remediation of soil or water.

16 Claims, 4 Drawing Sheets

Figure 1. Amplification sites of universal primers (not to scale).
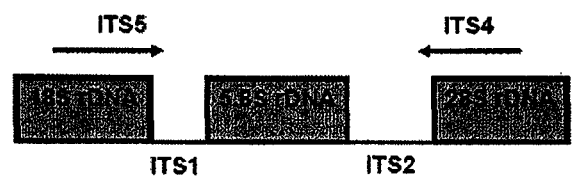
Figure 2. A schematic structure of EF-1α gene and location of primers used for amplification of different parts. From Druzhinina and Kubicek (2005).
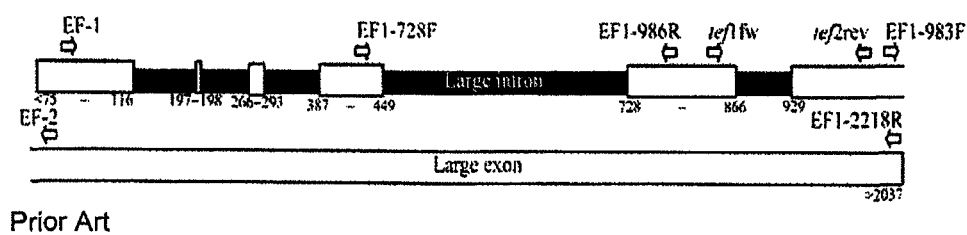
Prior Art Figure 3
A. Axenic tomato plants (left) and tomato plants inoculated with *Trichoderma harzianum* TSTh20-1 (right).
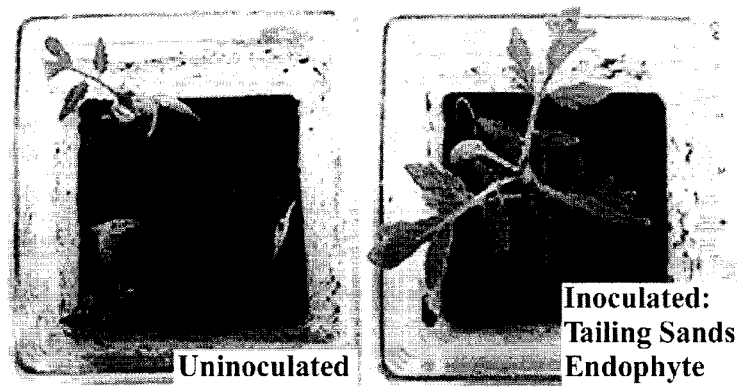
B. Average weight per plant for the experiment in A.
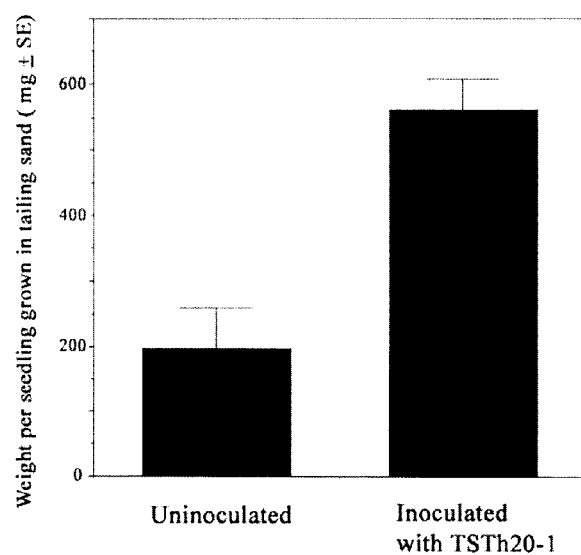

Figure 4. Histogram demonstrating the shoot length of 7-day old non-symbiotic (NS) and *Trichoderma* symbiotic (S) rice seedlings
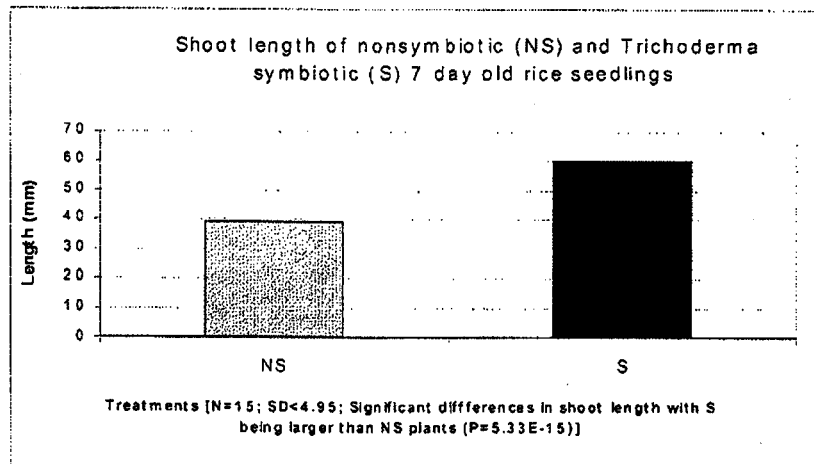
Figure 5. Histogram demonstrating the water use per gram of plant biomass for the same three corn varieties under non-symbiotic (NS) and *Trichoderma* symbiotic (S) conditions
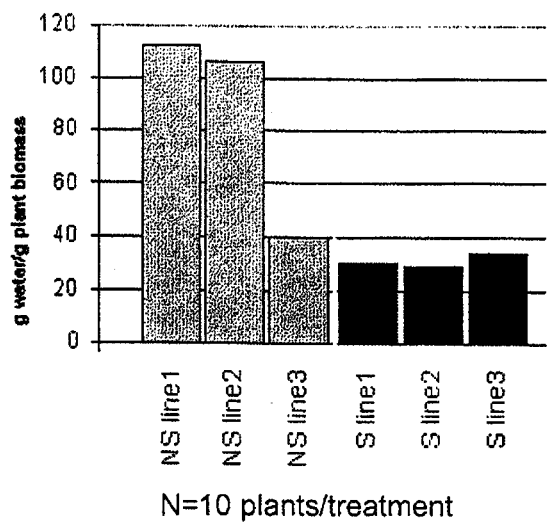
N=10 plants/treatment Figure 6. Histogram demonstrating the plant biomass for the three corn varieties depicted in Figure 3 for shoots (dark purple bars) and roots (light blue bars) under non-symbiotic (NS) and Trichoderma symbiotic (S) conditions
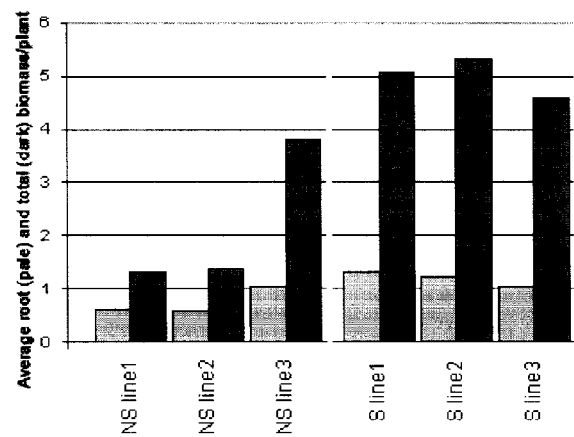

METHOD FOR INCREASING PLANT GROWTH USING THE FUNGUS *TRICHODERMA HARZIANUM*

This Patent Cooperation Treaty application claims the benefit of 35 USC 119 based on the priority of co-pending U.S. Provisional Patent Application 61/243,340, filed Sep. 17, 2009 which is incorporated herein in its entirety by reference.

FIELD

The present disclosure relates to a novel strain of *Trichoderma harzianum*, called TSTh20-1, for promoting plant growth, particularly under sub-optimal or stressful conditions with respect to water, organic carbon, nitrogen and mineral content, temperature, and contamination with polycyclic aromatic hydrocarbons or naphthenic acids.

BACKGROUND

Symbiosis is a mutually beneficial interaction between two organisms. Most plants are symbiotic with fungi (Petrini, 1986) and these fungi play important roles in the structure, function, and health of plant communities (Bacon and Hill, 1996; Clay and Holah, 1999; Petrini, 1986; Read, 1999; Rodriguez and Redman, 1997).

It has been demonstrated that a symbiotic relationship between plants and fungi can confer enhanced growth to host plants. For example, strains of endophytic fungi have conferred tolerance to host plants to extreme environmental conditions including high temperature, drought, and high salt content (Redman et al., 2002; Rodriguez et al., 2004; Rodriguez and Redman, 2008a; Rodriguez et al., 2009). In addition to promoting stress tolerance, endophytes also increase nutrient acquisition and growth rates of host plants, and enhance water use efficiency (Rodriguez et al., 2008; Rodriguez et al., 2009).

*Trichoderma harzianum* (*T. harzianum*) is a fungal species that encompasses a wide variety of physiologically specialized strains. Certain strains are used as biocontrol agents against soil-borne diseases of plants, and others are used for industrial production of cell wall degrading enzymes (Naseby et al., 2000). *Trichoderma harzianum* has been shown to induce metabolic changes in plants that increase their resistance to a wide variety of plant-pathogenic microorganisms and viruses (Harman et al., 2004). It has previously been shown that T-22, a particular strain of *Trichoderma harzianum*, can increase the growth of plant and root development under some conditions. T-22 can also solubilize plant nutrients for plant uptake that would otherwise be unavailable to plants in certain soils (Altomare et al., 1999; Harman et al., 2004).

Abiotic stress involves the negative impact of physical and chemical factors on living organisms such as temperature, water, pH, and nutrient limitation. Promoting plant growth in conditions of marginal to extreme abiotic stress would allow plants to become established in non-ideal environments, creating new vegetation. Creating new vegetation is important to soil remediation of polluted sites created by modern industry, agriculture, and other human activities.

The Athabasca oil sands in Alberta, Canada are the second largest in the world after Saudi Arabia. Oil sands contain bitumen, a semisolid mixture of complex hydrocarbons derived from coal or petroleum (Oil Sands Discovery Center, 2006) that are converted into synthetic crude oil. Oil sand surface-mining is damaging to the environment as it involves removal of trees and animals, and use of local water. About three cubic meters of liquid and solid tailings are produced per barrel of oil extracted. Current daily production from the oil sands, estimated at 1.5million barrels (240,000 cubic meters), would cover 100 football fields about knee-deep in tailing sands (TS). Since 1967, TS already cover more than 50 square kilometers to a far greater depth. The rate of extraction is forecast to double by 2020 and triple by 2030, See the world wide web at (.energy,gov.ab.ca/OilSands/oilsands.asp).

Tailing sands, the solid by-product of oil sand extraction, contain polycyclic aromatic hydrocarbons (PAHs) and naphthenic acids (NAs), which inhibit water absorption. Additionally, the oil extraction process removes much of the minerals and would also kill any soil microflora existed within the oil sands. This leaves the tailing sands deficient in minerals and flora. Thus, the tailing sands are challenging to support the plant life necessary to reclaim the sites.

Oil companies are expending considerable effort to overcome the challenges associated with tailings disposal and ultimate site reclamation (Matt Price, 2008). Traditional remediation methods of tailing sands are costly and time consuming. The cost of remediation per hectare now averages about $30,000 and it will take 15 years to remediate.

Compared to traditional methods (mixed fertilizer with plant material removed prior to surface mining, and stockpiled) bioremediation appears to be less labour intensive, and more environmentally safe since the tailing sand does not have to be covered with peat or other plant material, that must be taken from elsewhere. According to the reclaim standard, a reclaimed growing medium should be able to support a healthy plant community (similar to that of a comparable natural area) (Bois et al., 2006). Developing new vegetation on tailing sands is the key to a successful remediation.

SUMMARY

The inventors isolated a strain of endophytic fungus from a plant that was found growing on oil-sand tailings. The isolated fungus is from the species *Trichoderma harzianum*. Other strains of this species are already used in biotechnology applications, however, different strains have particular physiological characteristics for specialized uses.

One aspect of the disclosure provides an isolated *Trichoderma harzianum* strain TSTh20-1, which has been deposited at American Type Culture Collection under Patent Deposit Designation number PTA-10317 on Sep. 2, 2009, and its progeny and spores thereof, or an isolated culture thereof, or a mutant thereof having the ability to promote plant growth.

In another aspect, the disclosure provides a composition, comprising a *Trichoderma harzianum* strain TSTh20-1, and its progeny and spores thereof, or an isolated culture thereof, or a mutant thereof having the ability to promote plant growth, and, optionally, a carrier.

In still another aspect, the disclosure provides a method of promoting plant growth, comprising inoculating a plant with the *Trichoderma harzianum* strain TSTh20-1 described herein.

In yet another aspect, the disclosure provides a method of increasing water use efficiency of a plant, comprising inoculating a plant with the *Trichoderma harzianum* strain TSTh20-1 described herein.

In another aspect, the disclosure provides a method of remediation of soil or water, comprising inoculating a plant with the *Trichoderma harzianum* strain TSTh20-1 described herein, and growing said plant in the soil or water.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF DRAWINGS

FIG. 1 depicts the amplification sites of universal primers ITS5 and ITS4 that are used to amplify the targeted sequence ITS1-5.8S-IT2, also depicted. This drawing is not to scale.

FIG. 2 depicts a schematic structure of the translation elongation factor (EF-1α) gene of *H. jecorina* (GenBank accession number CAA80554) and location of primers used for amplification of different parts (Druzhinina and Kubicek, 2005).

FIG. 3A depicts the enhanced growth by tomato plant seedlings inoculated with *Trichoderma harzianum* TSTh20-1 on extracted tailing sands compared to non-inoculated tomato plant seedlings.

FIG. 3B depicts a histogram demonstrating the average total fresh weight (root plus shoot) for tomato seedlings grown on extracted tailing sands for two weeks and watered with distilled water.

FIG. 4 depicts a histogram demonstrating the shoot length of 7-day old non-symbiotic (NS) and *Trichoderma* symbiotic (S) rice seedlings.

FIG. 5 depicts a histogram demonstrating the water use per gram of plant biomass for the same three corn varieties under non-symbiotic (NS) and *Trichoderma* symbiotic (S) conditions.

FIG. 6 depicts a histogram demonstrating the plant biomass for the three corn varieties depicted in FIG. 3 for shoots (dark purple bars) and roots (light blue bars) under non-symbiotic (NS) and *Trichoderma* symbiotic (S) conditions.

DETAILED DESCRIPTION

The present disclosure relates to a *Trichoderma harzianum* fungal strain called TSTh20-1 that was isolated from plants growing on oil tailing sand sites. It has been shown that such fungal isolates are capable of promoting plant growth, particularly in conditions not ideal for growth, such as in oil tailing sands and in conditions where water is limited.

I. Definitions

The term "abiotic stress" as used herein refers to the negative impact of physical and chemical factors on living organisms in a specific environment. Physical and chemical factors can include, but are not limited to, water, organic nutrient levels, mineral nutrient levels, chemical contamination, temperature, rainfall, pH, oxygen content, hydrocarbon residues and alkali.

The term "endophyte" as used herein refers to a class of fungal symbionts that reside within host plant roots, stems and/or leaves, and that emerge during host senescence.

The term "inoculating a plant" with a fungus, for example, as used herein refers to applying or infecting a plant (including its roots, stem, leaves or seeds) with a fungus or fungal spores.

The term "TSTh20-1" refers to a fungal cell or culture that has been deposited at the American Type Culture Collection (ATCC) under Patent Deposit Designation number PTA10317 on Sep. 2, 2009.

The term "mutant of TSTh20-1" as used herein refers to a fungal cell that has undergone a mutation in its genetic code as compared to the TSTh20-1 strain, such as might be artificially created to enhance plant growth-related capabilities, to track the fungus in the plant, or to track the fungus in the environment to ensure consistency and provenance.

The term "oil tailing sands" or "tailing sands" as used herein refer to a by-product of the oil extraction process used in oil sand processing, such as, for example, the Athabasca oil sands.

The term "plant" as used herein includes any member of the plant kingdom that can be colonized by fungi. In one embodiment, the plant is an agricultural crop including, without limitation, tomato, rice, maize, watermelon, squash, turf and wheat. These plant species have been tested and TSTh20-1 has been shown to confer growth benefits to them.

The term "progeny of TSTh20-1" as used herein refers to all cells deriving from TSTh20-1 cells.

The term "promoting plant growth" as used herein means that the plant or parts thereof (such as roots and shoots) have increased in size or mass compared to a control plant, or parts thereof, that has not been inoculated with the fungus or as compared to a predetermined standard.

The term "remediation" as used herein refers to plant revegetation of environmental media and to the removal of pollution or contaminants from environmental media such as soil, groundwater, sediment, or surface water for the general protection of human health and the environment. In one aspect, the remediation is used for the revegetation of barren tailing sands.

The term "spores of TSTh20-1" as used herein refers to asexual reproductive cells formed by TSTh20-1 fungi, or its sexual stage, *Hypocrea*.

The term "symbiosis" and/or "symbiotic relationship" as used herein refer to a mutually beneficial interaction between two organisms including the interaction most plants have with fungi such as mycorrhizae. Similarly, the term "symbiont" as used herein refers to an organism in a symbiotic interaction.

The term "*Trichoderma harzianum* strain TSTh20-1" as used herein refers to the *Trichoderma harzianum* strain that has been deposited at American Type Culture Collection under Patent Deposit Designation number PTA10317 on Sep. 2, 2009.

The term "water use efficiency" as used herein means the amount of water consumed by plants over a defined period of time. It can also be defined by water use per gram of plant biomass.

As used herein, the terms "a" or "an" in relation to an object mean a representative example from a collection of that object.

The terms "unimpacted", "extracted", and "remediated" as used herein refer to sites or soil samples from sites that 1) were in the Athabasca oil sands region but had not been exploited for their bitumen content, 2) were tailing sands remaining after bitumen extraction, 3) had been remediated using conventional techniques, that is, covering with plant materials removed prior to surface mining and mixed with mineral fertilizer.

II. Isolated *Trichoderma harzianum* TSTh20-1

Under conditions of abiotic stress factors (including low mineral content, hydrocarbon residue, and high pH), pioneer plants such as *Taraxacum* (dandelion) and *Sonchus* (sowthistle) still colonize on tailing sands. Fungal endophyte cultures were isolated from samples of *Taraxacum* and *Sonchus* plants to examine the type found in the extracted, remediated, and unimpacted site samples. Once isolated from the plants, endophyte fungi were identified using morphological techniques and molecular techniques to amplify target DNA sequences were used to identify the specific genus and species. The inventors isolated one strain that they determined to be from *Trichoderma harzianum*.

In a first aspect, the disclosure provides an isolated *Trichoderma harzianum* strain TSTh20-1, which has been deposited at American Type Culture Collection (ATCC) under Patent Deposit Designation number PTA-10317 on Sep. 2, 2009, and its progeny and spores thereof, or an isolated culture thereof, or a mutant thereof having the ability to promote plant growth.

III. Compositions Comprising the Fungus TSTh20-1

Compositions for inoculating the plants with the *Trichoderma harzianum* strain TSTh20-1 described herein are also disclosed. In one aspect, the disclosure provides an inoculating composition, comprising a *Trichoderma harzianum* fungus TSTh20-1 or its progeny, spores or mutants thereof, and optionally a carrier. The composition may be applied to any part of the plant including roots, leaves, stems or seeds. The composition is preferably applied to dried seeds, most preferably as a dry seed coating.

In an embodiment, said composition is in a fluid form suitable for spray application or dip application. In another embodiment, said composition is in a paste-like form. In still another embodiment, said composition is in a substantially dry and powdered form for dusting. In yet another embodiment, said composition can promote plant growth. In another embodiment, said composition can promote plant growth under conditions of abiotic stress. In still another embodiment, said composition can promote plant growth on oil tailing sands. In yet another embodiment, said composition can increase water use efficiency of a plant. In yet another embodiment still, said composition can remediate soil or water. In another embodiment, said soil comprises oil tailing sands.

One of skill in the art can readily determine the amount or concentration of the composition that should be applied to the plant or plant seed to promote plant growth. In one embodiment, from about 5 to about 100,000 viable spores of the TSTh20-1 can be used per seed, preferably about 5 to about 500 viable spores per seed, more preferably less than 50 viable spores per seed.

IV. Methods and Uses of TSTh20-1

It has been shown that the fungal strain TSTh20-1 can promote plant growth, increase water use efficiency, and remediate soil.

1. a. Promoting Plant Growth

It is shown herein that the fungus TSTh20-1 has plant growth-promoting capabilities. For example, seedlings inoculated with TSTh20-1 have significantly longer shoots than seedlings not inoculated (see for example, Example 3). Enhanced plant growth has also been demonstrated upon inoculation of plant roots with TSTh20-1 in suboptimal conditions, including abiotic stress conditions. An example of abiotic stress conditions includes growth on contaminated soil such as seen on oil tailing sands (Example 2).

Therefore, in an aspect, the disclosure provides a method of promoting plant growth, comprising inoculating a plant with the TSTh20-1 strain described herein. In one embodiment, the method of promoting plant growth further comprises growing the plant in soil or water (that is, using hydroponic methods).

In another embodiment, the disclosure provides a use of a fungal composition to promote plant growth.

In an embodiment, the method of promoting plant growth occurs under conditions of abiotic stress. In another embodiment, the disclosure provides a use of TSTh20-1 strain to promote plant growth under conditions of abiotic stress. In an embodiment, the conditions of abiotic stress comprise the presence of polycyclic aromatic hydrocarbons (PAHs), napthenic acids (NAs), and/or high pH.

In another embodiment, the method of promoting plant growth occurs on oil tailing sands. In yet another embodiment, the disclosure provides a use of TSTh20-1 strain composition to promote plant growth on oil tailing sands.

Determining an improvement in plant growth using the TSTh20-1 fungus can be assessed in a number of ways. For example, the size or weight of the entire plant or a part thereof (such as shoots and roots) can be measured. In an embodiment, the average shoot length of an inoculated plant is increased at least 20% and as much as 60% fresh weight or dry weight. In another embodiment, rice plants inoculated with the *Trichoderma harzianum* strain TSTh20-1 have average shoot lengths that are at least 20% longer than rice plants that were not inoculated.

In still another embodiment, the method of promoting plant growth results in the mass of inoculated plants being about double the mass of the non-inoculated plants when grown on oil tailing sands.

b. Increased Water Use Efficiency

A demonstrated ability for endophyte fungi to increase the water use efficiency of a plant would be useful in drought resistance and allow better plant growth in conditions where water was limited. Herein, it is disclosed that the *Trichoderma harzianum* fungus TSTh20-1 has the ability to also improve the water use efficiency of a plant.

Therefore, in an aspect, the disclosure provides a method of increasing water use efficiency of a plant, comprising inoculating a plant with TSTh20-1 strain disclosed herein. In one embodiment, the method of increasing water use efficiency of this disclosure further comprises growing the plant in soil or water.

For example, corn plants inoculated with TSTh20-1 used significantly less water for growth than non-inoculated corn when water was limited, as seen in Example 4 and 5. Thus, in another embodiment, the inoculation with TSTh20-1 strain described herein causes plants to use up to 50% less water per gram of plant biomass. The inoculation with TSTh20-1 strain described herein inhibits plants from wilting when water is limiting. For example, wilting of inoculated plants occurs at about 18% moisture level, while non-inoculated plants wilt at about 23% moisture level. Accordingly, in an embodiment, inoculation with TSTh20-1 strain described herein allows a plant to survive on at least 25% less water.

c. Remediation

Oil companies have an interest in the oil sands, as they are an abundant source of crude oil. Alberta's oil sands are one of the few oil deposits in the world with growing production and about 176 billion barrels of proven oil reserves and a total recoverable oil reserve estimated to equal almost 335 billion barrels (Oil Sands Discovery Centre, 2006). However, tailing sand that is created as a by-product of the oil extraction process, poses environmental risks, including the migration of pollutants into groundwater and leakage into surrounding soil and surface water (Matt Price, 2008). Oil companies that use strip mining methods to extract oil are required to remediate the area to its original environmental condition once mining is completed. However, current remediation methods of tailing sands are costly and time consuming, and oil companies are expending considerable effort to overcome the challenges associated with tailings disposal and ultimate site reclamation. Therefore, a more suitable means of remediating oil tailing sands would be useful.

This disclosure provides that the isolated strain of fungal endophyte, *Trichoderma harzianum* TSTh20-1 is capable of allowing plant growth on oil tailing sands (Example 2), indicating that site reclamation is possible with this fungal strain.

Therefore, in an aspect, the disclosure demonstrates a method of remediation of soil or water comprising inoculating a plant with TSTh20-1 strain described herein, and growing said plant in the soil or water. In an embodiment, said soil or water comprises at least one pollutant, for example, polycyclic aromatic hydrocarbons (PAHs), naphthenic acids (NAs), and/or high pH. In another embodiment, said soil comprises oil tailing sands.

In another embodiment, the disclosure provides a use of TSTh20-1 strain to promote remediation of soil or water.

2. Inoculation Methods for Plants

It should be understood that the methods and uses described herein for plant inoculation apply to all methods and uses of the disclosure described, for example, for promoting plant growth, increased water use efficiency, and remediation of soil and water.

The plant can be inoculated with TSTh20-1 or a composition comprising TSTh20-1, using techniques known in the art. For example, the TSTh20-1 fungus or fungal spores may be applied to the roots of the plant, or to young germinated seedlings, or to ungerminated or germinated seeds. Furthermore, it is known in the art that other endophyte strains have been shown to be effective when spores are applied to ungerminated seeds. Therefore, in another embodiment, the fungus or fungal spores is applied to ungerminated seeds that give rise to a plant.

The methods described herein can be applied to any plant in need thereof. It is known that comparable endophyte strains of fungi readily colonize a wide diversity of plant species [Rodriguez et al 2008, 2009], and thus fungal inoculation with the strain described herein will colonize a variety of plant species. In one embodiment, the plant is an agricultural plant. In an embodiment, the agricultural plant can be rice, tomato, maize, watermelon, squash, turf and wheat, (currently under investigation; canola and soybean will be studied in the future, resources permitting). It is shown herein that TSTh20-1 fungal colonization occurs in tomato, rice, and corn plants, as in Examples 2-4, and we have experimental evidence for comparable growth enhancement by TSTh20-1 for additional agricultural crops, including beans, wheat, turf, squash, radish. Thus, in still another embodiment, the agricultural plant is selected from tomato plants, rice plants, maize plants, watermelon plants, squash plants, turf and wheat. In another embodiment, the agricultural plant is a tomato plant. In still another embodiment, the agricultural plant is a rice plant. In yet another embodiment, the agricultural plant is a corn plant.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present application:

EXAMPLES

Example 1

Isolation of *Trichoderma harzianum* strain TSTh20-1

Fungal strains were isolated from surface-sterilized plants that had been collected from tailing sands sites, and then cultured on 10% potato dextrose agar at 28 C for 4-10 d, eventually producing a mixture of species. Fungal colonies that grew out from these plant samples were purified to by standard methods. Purified cultures were tested for their ability to confer tolerance to growth on tailing sands using tomato as a test plant species. Only TSTh20-1 of four genera and multiple isolates of endophtye fungi was able to confer the specified tolerance.

Fungi colonizing *Taraxacum* and *Sonchus* plants growing on oil tailing sands in Alberta, Canada were obtained and isolated using techniques known in the art. The strains of isolated fungi were then identified using morphological and molecular techniques.

a. Molecular Identification of Endophytic Fungi i. Target DNA Sequences

The internal transcribed spacer (ITS) region of fungal rDNA genes has been identified by previous studies as suitable targets for molecular analysis of fungal identification (Bridge and Spooner, 2001; Gardes and Bruns, 1993). ITS regions are stretches of DNA that are located between the 18S and 5.8S ribosomal DNA (rDNA) coding regions (ITS1) and between the 5.8S and 28S rDNA coding regions (ITS2) (Bakker et al., 1994) (FIG. 1). The ITS region has a high degree of variation because of the relatively low evolutionary pressure acting on these non-functional sequences. Their highly varied sequence relative to the conserved flanking rDNA genes in fungi and the high copy number of rDNA genes makes it to be easy to amplify even from small quantities of DNA (Buchan et al., 2002). Here, the ITS sequence data were used as the complement of morphological methods to identify the endophyte fungi strains at genus level.

To identify the *Trichoderma* strain to species level, an approximately 0.65 kb fragment of the protein coding translation elongation factor gene (EF-1α) (FIG. 2), 0.5 kb section calmodulin gene (cal), and 0.75 kb actin gene (act) were amplified and sequenced. To combine the ITS sequence, EF-1α sequence, cal sequence, and act sequence information together provides much greater resolution of the representatives of *Trichoderma* spp. compared to what ITS sequence supplies (Samuels et al., 2006) and makes it possible to identify the *Trichoderma* strain to species level accurately.

ii. Primer Design

The primer pair ITS4 and ITS5 is universal primer pair used for the amplification of the ITS1-5.8S-ITS2 target sequence (White et al., 1990) (FIG. 1). O'Donnell et al. (1998) designed primer pair EF-1 and EF-2 to amplify translation elongation factor coding region (EF-1α) from *Fusarium* spp. Then primer pair EF1-728F and TEF1 rev was applied in amplification of EF-1α coding region in *Trichoderma* spp and showed positive results (Samuels et al., 2002). CAL-228F and CAL-737R primer pair were designed to amplify calmodulin gene in filamentous fungi by Carbone and Kohn in 1999, then used in identification of *Trichoderma* spp by Chaverri et al. (2002). Tact1 and Tact2 primer pair were designed and successfully used for amplifying actin gene in *Trichoderma* spp by Samuels et al. in 2006.

b. Morphological and Quantification Studies

Lactofuchsin (LF) is used in the staining of plant samples to study the morphology of AMF and fungal endophytes as LF can bind to chitin, a component of most fungal walls (Bevege, 1968; Kormanik et al., 1980). LF has a wide range of excitation wavelengths, spanning at least 405-534 nm (blue to green) available with most epifluorescence systems (Kaminskyj, 2008). To study the morphological structure of fungi inside of plant tissue confocal laser scanning microscopy (CLSM) can be used. When using CLSM, plant samples are cleared of cytoplasm and then stained in acid fuchsin in lactic acid, followed by a destaining step (Allen et al., 2006; Ormsby et al., 2007; Kaminskyj, 2008). Slides are imaged at a specific excitation related to the fluorescent stain. CLSM is able to scan at different focal depths, making it much easier to locate fungal structures within the host root.

Wide field epifluorescent microscopy can be used for quantification of fungi colonization within plant tissue, while synchrotron mid-infrared spectroscopy can be used to assess the biochemical composition of fungal endophytes in pure culture. When using epifluorescence, since the LF stain is a very stable fluorochrome, photobleaching is seldom a problem (Kaminskyj, 2008). Wide field epifluorescence microscopy lights up the entire field, provides an improved signal to noise ratio and is an efficient and flexible method for quantification (Kaminskyj, 2008).

Example 2

Effect of *Trichoderma harzianum* strain TSTh20-1 on Tomato Plant Seedling Growth in Extracted Tailing Sands Tomato seeds were grown in double-decker magenta boxes containing sterile potting mix in the upper chamber, and mineral nutrient solution (as is known in the art) in the lower chamber. At two weeks, seedlings were gently removed from the potting mix, and inoculated as described below, and transplanted into tailing sand. The lower chamber was filled with sterile distilled water, and grown under the same conditions of temperature, moisture and light. FIG. 3A shows the effect of two weeks of growth on tailing sands by established seedlings (left) uninoculated plants, and (right) a plant inoculated with *T. harzianum* strain TSTh20-1 from a plant that had naturally colonized tailing sand. Inoculated and control seedlings were grown for an additional two weeks (four in all) before assessing growth.

Tailing sands are the solid waste produced following bitumen extraction from tar sand deposits. The tailing sands have extremely low available mineral content, particularly for phosphorous (0.1 ppm), calcium (4.3 ppm), magnesium (1.0 ppm). Tailing sands also have low organic carbon (0.2%), high pH (8.3), and are hydrophobic, likely due to residual hydrocarbons.

When the plants were grown for two weeks on extracted tailing sand and watered with distilled water, the symbiont-colonized tomato seedlings had significantly greater average, about double, total fresh weight (root plus shoot) than the non-colonized plants, as indicated in FIGS. 3A and 3B. Symbiont-colonized plants also had significantly greater dry weight when compared to non-colonized plants. Preliminary tests have shown that inoculated tomato seedlings also demonstrated greater wilt resistance, and more rapid recovery following wilting.

This example indicated that TSTh20-1 inoculation enhances plant growth in oil tailing sands, conditions of not ideal for plant growth.

Example 3

The Effect of *Trichoderma harzianum* TSTh20-1 on Growth of Paddy Rice

Rice plant seedlings were grown in potting mix with a mineral nutrient solution for two weeks. Seedlings were either inoculated with TSTh20-1 or a sterile water control. After 7 days of growth, rice seedlings colonized with TSTh20-1 had significantly longer shoots than non-symbiotic seedlings (p=5.33 E-15), as depicted in FIG. 4. Rice seedlings were grown in nutrient-free water agar; additional trials were in sterile soil.

Growth enhancement due to the TSTh20-1 treatment effect is attributable to more rapid root development in the symbiotic seedlings, leading to enhanced shoot growth. Enhanced plant growth is correlated to increased drought tolerance seen in symbiotic seedlings.

Example 4

The Effect of *Trichoderma harzianum* TSTh20-1 on Water Use by Three Varieties of Maize The roots of three corn varieties were inoculated with TSTh20-1 spores. Ten inoculated seedlings and five non-inoculated seedlings were grown for two weeks in fertilized growing medium. Water use was measured as the total volume consumed (mL) by plants over a 10 day period. There were significant difference in the amount of water consumed/plant biomass with symbiotic (two of the three varieties) using substantially less water than nonsymbiotic plants (FIG. 5).

Example 5

The Effect of *Trichoderma harzianum* TSTh20-1 on Plant Biomass for Three Varieties of Corn The three varieties of corn described in Example 4 were analyzed for biomass. As indicated in FIG. 6, both the shoots (dark purple bars) and roots (light blue bars) have enhanced biomass in TSTh20-1-colonized plants compared to non-symbiotic plants. This effect is very significant for corn lines 1 and 2. Line 3, which had the best performance under non-symbiotic conditions, also had greater shoot biomass with the *Trichoderma* symbiosis.

Example 6

The Effect of *Trichoderma harzianum* TSTh20-1 on Tomato Plant Drought Resistance The roots of axenic tomato plant seedlings were inoculated with TSTh20-1 spores. Five inoculated seedlings and five non-inoculated seedlings were grown for two weeks in mineral nutrient-fertilized growing medium, as is know in the art. After two weeks, the growing medium was allowed to dry and the water content of the growing medium was determined for each plant at the onset of wilting. This was done at US.

Wilting of inoculated tomato plants occurred at about 18% moisture, while wilting of non-inoculated plants occurred at about 23% moisture.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents, and patent applications are herein incorporated by reference in their entirety to the same extent as if each individual publication, patent or patent application was specifically and individually indicated to be incorporated by reference in its entirety.

REFERENCES

Allen N, Nordlander M, McGonigle T, Basinger J, Kaminskyj S 2006 Arbuscular mycorrhizas on Axel Heiberg Island (80° N) and at Saskatoon (52° N) Canada. Can J Bot 84: 1094-1100

Altomare, C., Norvell, W. A., Björkman, T. & Harman, G. E. (1999) Solubilization of phosphates and micronutrients by the plant-growth-promoting and biocontrol fungus *Trichoderma harzianum* Rifai 1295-22. Appl. Environ. Microbiol. 65: 2926-2933.

Bacon, C. W. & Hill, N. S. 1996. Symptomless grass endophytes: products of coevolutionary symbioses and their role in the ecological adaptations of grasses. in S. C. Redkin & L. M. Carris (ed.), *Endophytic Fungi in Grasses and Woody Plants*, St. Paul, APS Press, pp. 155-178.

Bakker F T, Olsen J L, Stam W T, van den Hoek C (1994) The Cladophora complex (Chlorophyta): new views based on 18S rRNA gene sequences. Molec Phylogenet Evolut 3(4): 365-382.

Bevege, D. I. (1968) A rapid technique for clearing tannins and staining intact roots for detection of mycorrhizas caused by *Endogone* spp., and some records of infection in Australasian plants. Trans. Br. Mycol. Soc. 551: 808-810.

Bois, G., A. Bertrand, A., Piché, Y., Fung, M. & Khasa D. P. (2006) Growth, compatible solute and salt accumulation of five mycorrhizal fungal species grown over a range of NaCl concentrations. Mycorrhiza 16: 99-109.

Bridge, P. & Spooner, B. (2001) Soil fungi: diversity and detection. Plant and Soil 232: 147-154.

Clay, K. & Holah, J. 1999. Fungal endophyte symbiosis and plant diversity in successional fields. Science, 285:1742-1744.

Druzhinina, I. & Kubicek, C. P. (2005) Species concepts and biodiversity in *Trichoderma* and Hypocrea: from aggregate species to species clusters? J Zhejiang Univ Sci 6:100-112

Gardes, M. & Bruns, T. D. (1993) ITS-RFLP matiching for species identification in fungi. Methods in Molecular Biology 50: 177-186.

Harman, G. E., Howell, C. R., Viterbo, A. , Chet I. & Lorito, M. (2004) *Trichoderma* species—opportunistic, avirulent plant symbionts. Nat. Rev., Microbiol. 2: 43-56.

Kaminskyj SGW 2008 Effective and flexible methods for visualizing and quantifying endorhizal fungi. In Mycorrhizae: Sustainable Agriculture and Forestry (Z A Siddiqui, M S Akhtar, K Futai, Editors). Springer-Verlag, Dordrecht, The Netherlands. Pages 337-349.

Kormanik, P. P., W. Craig Bryan, W. C. & Schultz, R. C. (1980) Procedures and equipment for staining large numbers of plant root samples for endomycorrhizal assay. Can. J. Microbiol. 26: 536-538

Naseby, D. C., Pascual, J. A. and Lynch, J. M. (2000) 'Effect of biocontrol strains of *Trichoderma* on plant growth, Pythium ultimum populations, soil microbial communities and soil enzyme activities.' Journal of Applied Microbiology 88 (1) pp.161-169

O'Donnell, K. L., Cigelnik, E. & Nirenberg, H. I. (1998) Molecular systematics and phylogeography of the *Gibberella fujikuroi* species complex. Mycologia 90: 465-493.

Oil Sands Discovery Centre. (2006) http://www.oilsandsdiscovery.com/

Ormsby A, Hodson E, Li Y, Basinger J, Kaminskyj S 2007 Arbuscular mycorrhizae associated with Asteraceae in the Canadian High Arctic: the value of herbarium archives. Can J B 85: 599-606.

Petrini, O. 1986, Taxonomy of endophytic fungi of aerial plant tissues. in N. J. Fokkema & J. van den Heuvel (ed.), *Microbiology of the Phyllosphere*, Cambridge, Cambridge University Press, pp. 175-187.

Read, D. J. 1999. Mycorrhiza—the state of the art. In A. Varma & B. Hock (ed.), Mycorrhiza, Berlin, Springer-Verlag, pp. 3-34.

Redman, R. S., Sheehan, K. B., Stout, R. G., Rodriguez, R. J. and Henson, J. M. 2002. Thermotolerance Conferred to Plant Host and Fungal Endophyte During Mutualistic Symbiosis. Science, 298:1581.

Rodriguez, R. J. & Redman, R. S. 1997. Fungal life-styles and ecosystem dynamics: biological aspects of plant pathogens, plant endophytes and saprophytes. *Advances in Botanical Research*, 24:169-193.

Rodriguez, R. J., Redman R. S., and Henson, J. M. 2004. The Role of Fungal Symbioses in the Adaptation of Plants to High Stress Environments. *Mitigation and Adaptation Strategies for Global Change*, 9:261-272.

Rodriguez R. J., Henson J., Van Volkenburgh E., Hoy M., Wright L., Beckwith F., Kim Y., Redman R. S. 2008a. Stress Tolerance in Plants via Habitat-Adapted Symbiosis. *ISME-Nature*, 2:404-416.

Rodriguez R. J. and Redman R. S. 2008b. More Than 400 Million Years Of Evolution And Some Plants Still Can't Make It On Their Own: Plant Stress Tolerance Via Fungal Symbiosis. *Journal of Experimental Botany*, 59:1109-1114.

Rodriguez R J, Freeman D C, McArthur E D, Kim Y O, Redman R S. 2009. Symbiotic Regulation Of Plant Growth, Development And Reproduction. *Communicative & Integrative Biology*, 2(2): 1-3.

Rodriguez R J, White J F J, Arnold A E, Redman R S. 2009. Fungal endophytes: diversity and functional roles. *Tansley Review, New Phytologist*. 182(2):314-30.

White, T. J., T. Bruns, S. Lee, and J. Taylor. 1990. Amplification and direct sequencing of fungal ri-bosomal RNA genes for phylogenetics. Pp. 315-322. In: PCR protocols: a guide to methods and applications. Eds., M. A. Innis, D. H. Gelfand, J. J. Sninsky, and T. J. White. Academic Press, New York.

The invention claimed is:

1. An isolated *Trichoderma harzianum* strain TSTh20-1, which has been deposited at America Type Culture Collection under Patent Deposit Designation number PTA-10317 on Sep. 2, 2009 and its progeny and spores thereof.

2. A composition comprising an isolated *Trichoderma harzianum* fungus TSTh20-1 and its progeny and spores thereof and, optionally, a carrier.

3. The composition of claim 2, which is in a fluid form suitable for spray application or dip application or for coating seeds.

4. The composition of claim 2, which is in a paste-like form.

5. The composition of claim 2, which is in a substantially dry and powdered form for dusting.

6. A method of promoting plant growth, comprising inoculating a plant with the isolated TSTh20-1 of claim 1.

7. The method of claim 6, wherein the plant growth occurs under conditions of abiotic stress.

8. The method of claim 7, wherein the conditions of abiotic stress comprise the presence of polycyclic aromatic hydrocarbons (PAHs), napthenic acids (NAs), or a pH of at least 8.3.

9. A method of increasing water use efficiency of a plant, comprising inoculating a plant with the isolated TSTh20-1 of claim 1.

10. The method of claim 7, further comprising growing said plant in soil or water.

11. A method of remediation of soil or water, comprising inoculating a plant with the isolated TSTh20-1 of claim 1.

12. The method of claim 11, wherein the soil or water comprises polycyclic aromatic hydrocarbons (PAHs), napthenic acids (NAs), or a pH of at least 8.3.

13. The method of claim 7, wherein the plant growth occurs on oil tailing sands.

14. The method of claim 6, wherein the plant inoculated is an agricultural plant.

15. The method of claim 14, wherein the agricultural plant is selected from the group of plants comprising tomato plants, rice plants, maize plants, watermelon plants, squash plants, turf and wheat.

16. The method of claim 6, wherein said fungus is applied to an ungerminated seeds that will give rise to said plant.

* * * * *